United States Patent [19]
Haelsig et al.

[11] Patent Number: 5,523,511
[45] Date of Patent: Jun. 4, 1996

[54] HIGHLY SELECTIVE N-OLEFIN ISOMERIZATION PROCESS USING LOW ZEOLITE CONTENT ZSM-35 CATALYST

[75] Inventors: Claus-Peter Haelsig, Irvine, Calif.; Albin Huss, Jr., Chadds Ford, Pa.; Donald J. Klocke, Somerdale, N.J.; Daria N. Lissy, Glen Mills, Pa.; Iraj I. Rahmim, Voorhees, N.J.

[73] Assignee: Mobil Oil Corporation, Fairfax, Va.

[21] Appl. No.: 228,779

[22] Filed: Apr. 18, 1994

Related U.S. Application Data

[63] Continuation-in-part of Ser. No. 962,637, Oct. 16, 1992, abandoned, which is a continuation-in-part of Ser. No. 760,287, Sep. 16, 1991, abandoned.

[51] Int. Cl.⁶ .................................................. C07C 5/27
[52] U.S. Cl. .................................................. 585/671
[58] Field of Search .................................................. 585/671

[56] References Cited

U.S. PATENT DOCUMENTS

| | | | |
|---|---|---|---|
| 3,992,466 | 11/1976 | Plank et al. | 585/467 |
| 4,886,925 | 12/1989 | Harandi | 585/331 |
| 4,922,048 | 5/1990 | Harandi | 585/310 |
| 4,996,386 | 2/1991 | Hamilton, Jr. et al. | 585/646 |
| 5,321,194 | 7/1994 | Apelian et al. | 585/671 |

FOREIGN PATENT DOCUMENTS

| | | |
|---|---|---|
| 0026041 | 4/1981 | European Pat. Off. . |
| 0247802 | 6/1990 | European Pat. Off. . |
| 0012185 | 5/1986 | United Kingdom . |
| 93023353 | 11/1993 | WIPO . |

Primary Examiner—Ponnathapura Achutamurthy
Attorney, Agent, or Firm—Alexander J. McKillop; Dennis P. Santini; Laurence P. Hobbes

[57] ABSTRACT

A process is disclosed for the highly selective skeletal isomerization of linear olefin-containing organic feeds to iso-olefins at high levels of feed conversion wherein linear olefins, e.g., n-butenes, are contacted with catalyst comprising ZSM-35 under skeletal isomerization conditions which can include temperatures of 100° to 750° C. and linear olefin space velocities of less than 30 WHSV. The process uses a catalyst composition comprising 5 to 40 wt % ZSM-35, and 60 to 95 wt % inorganic oxide matrix, e.g., silica.

18 Claims, 5 Drawing Sheets

HIGHLY SELECTIVE N-OLEFIN ISOMERIZATION PROCESS USING LOW ZEOLITE CONTENT ZSM-35 CATALYST

REFERENCE TO COPENDING APPLICATION

This application is a continuation-in-part of U.S. patent application Ser. No. 07/962,637, filed Oct. 16, 1992, now abandoned, which in turn is a continuation-in-part of U.S. patent application Ser. No. 07/760,287, filed Sep. 16, 1991, now abandoned, the entire contents of which are incorporated herein by reference.

FIELD OF THE INVENTION

This invention relates to a method for the catalytic conversion of n-olefin-containing, e.g., n-butene-containing, hydrocarbon streams to iso-olefin-rich, e.g., isobutene-rich product streams under skeletal isomerization conditions, with a zeolite catalyst.

BACKGROUND OF THE INVENTION

The demand for iso-alkenes has recently increased. For example, relatively large amounts of isobutene are required for reaction with methanol or ethanol over an acidic catalyst to produce methyl tert-butyl ether (MTBE) or ethyl tert-butyl ether (ETBE) which is useful as an octane enhancer for unleaded gasolines. Isoamylenes are required for reaction with methanol over an acidic catalyst to produce tert-amyl methyl ether (TAME). With passage of the Clean Air Act in the United States mandating increased gasoline oxygenate content, MTBE, ETBE and TAME have taken on new value as clean-air additives, even for lower octane gasolines. Lead phasedown of gasolines in Western Europe has further increased the demand for such oxygenates.

An article by J. D. Chase, et al., *Oil and Gas Journal*, Apr. 9, 1979, discusses the advantages one can achieve by using such materials to enhance gasoline octane. The blending octane values of MTBE when added to a typical unleaded gasoline base fuel are RON=118, MON=101, R+M/2=109. The blending octane values of TAME when added to a typical unleaded gasoline base fuel are RON=112, MON=99, R+M/2=106. Isobutene (or isobutylene) is in particularly high demand as it is reacted with methanol to produce MTBE.

The addition of shape-selective zeolite additives such as ZSM-5 to cracking catalysts, e.g., those used in fluidized catalytic cracking (FCC), is beneficial in producing gasoline boiling range product of increased octane rating. However, increased amounts of olefins result, including n-butenes, creating a need for their conversion to higher value products such as isobutene which can be used to produce MTBE.

Butene exists in four isomers: butene-1, cis-butene-2, its stereo-isomer trans-butene-2, and isobutene. Conversions between the butenes-2 is known as geometric isomerization, whereas that between butene-1 and the butenes-2 is known as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_4$ or $C_4+$ crackate used to produce tertiary alkyl ethers in the prior art which contains normal butene and isobutene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites in the restructuring of olefins.

European Patent 0026041 to Garwood, incorporated herein by reference, discloses a process for the restructuring of olefins in contact with zeolite catalyst to produce iso-olefins, followed by the conversion of iso-olefins to MTBE and TAME. The restructuring conditions comprise temperature between 204° C. and 315° C. and pressure below 51 kPa.

In European Patent 0247802 to Barri et al., it is taught that linear olefins can be restructured in contact with zeolite catalyst, including Theta-1 (ZSM-22) and ZSM-23, to produce branched olefins. The restructuring conditions comprise temperature between 200°–550° C., pressure between 100 and 5000 kPa and WHSV between 1 and 100. Selectivities to isobutene up to 91.2% are reported using a calcined Theta-1 tectometallosilicate at 400° C. and 30.6% 1-butene conversion.

U.S. Pat. No. 3,992,466 to Plank et al. teaches the use of ZSM-35 as a catalyst for hydrocarbon conversion reactions, including "isomerization of aromatics, paraffins and olefins."

U.S. Pat. No. 4,922,048 to Harandi discloses the use of a wide variety of medium pore size zeolites, e.g., ZSM-5, ZSM-11, ZSM-12, ZSM-22, ZSM-23, ZSM-35 and ZSM-48, in low temperature (232°–385° C.) olefin interconversion of $C_2$–$C_6$ olefins to products including tertiary $C_4$–$C_5$ olefins and olefinic gasoline.

U.S. Pat. No. 4,886,925 to Harandi discloses low pressure high temperature conversion of light olefins to produce higher olefins rich in isoalkenes. The process converts $C_{2+}$ n-alkenes to a product comprising $C_4$–$C_6$ alkenes rich in iso-alkenes, $C_7+$ olefinic gasoline boiling range hydrocarbons, and unconverted hydrocarbons over ZSM-5. The reference teaches further treatment of the alkene effluent with methanol in the presence of medium pore size zeolites such as ZSM-5, ZSM-11, ZSM-12, ZSM-35, ZSM-38 and ZSM-48.

U.S. Pat. No. 4,996,386 to Hamilton, Jr. discloses concurrent isomerization and disproportionation of hydrocarbon olefins using a ferrierite/Mo/W/$Al_2O_3$ catalyst. The catalyst exemplified produces fewer branched olefins than a comparable material free of ferrierite and the reference teaches that ferrierite-containing catalysts exhibit improved selectivity to linear olefins than conventionally prepared disproportionation catalysts.

All of the above references are incorporated herein by reference.

Despite the efforts exemplified in the above references, the skeletal isomerization of olefins e.g., to produce isobutene, has been hampered by relatively low conversion and/or selectivity to isobutene perhaps owing to the lability of these olefins. It is further known that skeletal isomerization becomes more difficult as hydrocarbons of lower molecular weight are used, requiring higher temperatures and lower linear olefin partial pressures.

Generally, the conversion of n-butenes to iso-butene is conducted at selectivities below 90%. In order to obtain higher selectivities, operation at high temperatures (>500° C.) and with high feed dilution (butene partial pressure, typically less than 5 psia (34.5 kPa)) is generally required. Selectivities of greater than 85%, 90%, 95% or even 99% are highly advantageous in commercial conversion of n-butenes to isobutene in order to avoid the need to separate out materials other than n-butene from the product stream. Such high selectivities will permit direct (cascading) or indirect introduction of the isomerizer effluent to an etherification zone where isobutene is reacted with alkanol to produce alkyl tert-butyl ether, e.g., MTBE. Unconverted n-butenes in the isomerizer effluent can be withdrawn either before the etherification zone or preferably, from the etherification zone effluent insofar as the etherification reaction utilizes only the isobutene component of the isomerizer stream. Unreacted n-butenes from the etherification zone effluent can be recycled to the isomerizer where they are converted to isobutene at high selectivity. If the recycle stream contains not only unconverted linear olefins, e.g., n-butenes, but also by-products such as other olefins (e.g., propylene) or paraffins, they have to be removed from the recycle stream, such as by distillation or by taking a slip stream. These removal steps are expensive and can lead to considerable loss of not only the by-products but butenes as well. These losses are larger when the by-products formed are present in higher concentration. Thus, even small improvements in the isobutene selectivity during n-butene isomerization have a major effect on the commercial viability of the process.

Further enhancement of total yield of iso-olefin can be effected by enhancing overall conversion of the n-olefin-containing feedstream. With this object in mind, it would be advantageous to provide a skeletal isomerization catalyst capable of maintaining a high level of conversion as well as high iso-olefin selectivity, even at relatively low temperatures, e.g., no greater than 450° C. and high n-olefin space velocities. ZSM-35 catalysts comprising zeolite loadings of 50 wt % or higher and inorganic oxide binder have been found useful for this process. However, such catalysts have relatively high activity and therefore require relatively high linear olefin WHSV operation, e.g., (30–60).

Skeletal isomerization of linear olefins has been characterized as being favored at relatively low linear olefin partial pressures, e.g., less than one atmosphere. This can be done by diluting the linear olefin-containing feed with a suitable diluent, e.g., nitrogen. In order to provide a commercially acceptable overall conversion rate, other process parameters can be adjusted, e.g., increasing the space velocity of the diluted feed to the reactor. However, increasing space velocity to a level sufficient to provide acceptable overall conversion can bring on attendant high pressure drops which can create additional problems, especially where the olefin skeletal isomerization catalyst selectivity to iso-olefins is sensitive to changes in pressure, as is the case with catalyst comprising relatively high levels of ZSM-35.

Accordingly, it would be useful to find a way of reducing olefin space velocity in order to minimize pressure drop effects. It would also be useful to provide an olefin skeletal isomerization catalyst which is relatively insensitive to changes in linear olefin partial pressure caused by reactor pressure drops, which would allow operation at higher space velocities and a broader range of linear olefin partial pressures resulting in a larger operating window.

SUMMARY OF THE INVENTION

The present invention provides a method for conversion of linear olefins to corresponding iso-olefins which comprises contacting a linear olefin-containing organic feedstock with a catalyst composition comprising a zeolite having the structure of ZSM-35 under skeletal isomerization conditions, wherein said catalyst composition comprises 5 to 40 wt %, say 5 to 25 wt %, of said zeolite, and 60 to 95 wt %, say 75 to 95 wt %, inorganic oxide matrix material, e.g., silica.

A catalyst composition which comprises minor amounts of zeolite and major amounts of inorganic oxide matrix material is significantly less active in olefin skeletal isomerization than higher zeolite content catalyst, thereby permitting operation at lower space velocity, which avoids unwanted pressure drops. Moreover, the iso-olefin selectivity of such catalyst has unexpectedly been found to be relatively insensitive to partial linear olefin pressure changes which permits operation over a wide range of linear olefin partial pressures, including high partial pressures of at least 101.3 kPa (1 atmosphere), e.g. from 101.3 to 202.6 kPa (1 to 2 atmospheres) or even higher, say 101.3 to 303.9 kPa (1 to 3 atmospheres). In addition, the lower zeolite content catalyst unexpectedly exhibits significantly higher iso-olefin selectivities than higher zeolite content catalysts. Finally, the catalyst of the present invention exhibits a lower end-of-cycle coke level as compared to higher zeolite content catalyst. This advantageously results in significantly reduced regeneration requirements.

The high iso-olefin selectivity of ZSM-35 in the present invention results in large part from isomerization occurring without significant conversion to lighter and heavier molecules. This phenomenon, it is believed, is a consequence of the pore structure of ZSM-35 which promotes isomerization at a much faster rate than the reaction by which say, butene, is converted to lighter (mostly propene) and heavier olefins (olefin interconversion reaction). Moreover, such isomerization takes place without significant cracking of the feed or hydrogenation or dehydrogenation effects resulting in the formation of, say, n-butane or butadiene. The present invention can be used to effect conversion of linear olefins to iso-olefins while resulting in less than 30%, 10%, or even less than 5% by weight of converted product having lower or higher average carbon number.

In one aspect, the present invention can provide enhanced overall yields of iso-olefin product from linear olefin-containing feeds by a highly selective conversion of linear olefins to corresponding iso-olefins of the same carbon number, e.g., n-butenes to isobutene, or linear pentenes to isopentenes, at enhanced linear olefin conversion levels.

The present invention's utilization of low zeolite content ZSM-35 catalyst results in highly selective conversion of n-olefins to iso-olefins even at lower linear olefin space velocities, i.e., less than 30 WHSV, e.g., 5 to 25 WHSV, as well as conversion of n-olefin feed at significantly higher levels, over a broad temperature range, particularly at temperatures of less than about 500° C., 450° C. or even 400° C., as well as over a broad linear olefin partial pressure range. Moreover, in another aspect of the invention, the relative insensitivity of the iso-olefin selectivity of the catalyst to changes in linear olefin partial pressure of the low content zeolite catalyst permits greater operation flexibility.

DETAILED DESCRIPTION OF THE INVENTION

The skeletal isomerization reaction of the present invention is carried out at temperatures between 100° and 750° C.; weight hourly space velocity based on linear olefin in the feed between 0.1 and 500 WHSV; and linear olefin partial pressure between 2 and 2000 kPa. The preferred conditions are temperatures between 150° and 600° C., more preferably between 250° and 500° C., say between 350° and 500° C., WHSV between 0.5 and 400, more preferably less than 30, e.g., between 5 and 30; and a linear olefin partial pressure between 10 and 500 kPa, more preferably between 20 and 200 kPa.

The present invention is especially suited to processes carried out at high linear olefin to iso-olefin selectivity, e.g., at least 60% at relatively low conversion temperatures and high linear olefin partial pressures. Such processes can maintain selectivities of at least 75, 85, 90 or even 95% at a conversion temperature less than or equal to: 550°, 450°, 400° or even 350° C., and linear olefin partial pressures above 2 psia (14 kPa), e.g., above 5 psia (34 kPa), or even above 14.7 psia (100 kPa), say 14.7 to 29.4 psia (100 to 200 kPa). Such processes can be carried out at an overall conversion of linear olefins of at least 25, 30, 35, 40, or 45 wt % or higher. The present method is particularly effective when operating at lower temperatures, e.g., less than 450° C.

Preferred feedstreams for use in the present invention include $C_4$ or $C_4+$ hydrocarbon feedstreams. Linear olefins suited to use in the present invention may be derived from a fresh feedstream, preferably comprising n-butenes and/or n-pentenes, or from the effluent of an iso-olefin etherification reactor which employs alkanol and $C_4$ or $C_4+$ hydrocarbon feedstock. Typical hydrocarbon feedstock materials for isomerization reactions according to the present invention include olefinic streams, such as cracking process light gas containing butene isomers in mixture with substantial amounts of paraffins including n-butane and isobutane. The $C_4$ components usually contain a major amount of unsaturated compounds, such as 10–40% isobutene, 20–55% linear butenes, and small amounts of butadiene. Also, $C_4+$ heavier olefinic hydrocarbon streams may be used, including $C_4$ to $C_{10}$, preferably $C_4$ to $C_6$ olefinic hydrocarbon streams, e.g., $C_5$ or $C_5+$ olefinic hydrocarbon streams, e.g., light FCC gasoline. Feedstocks comprising at least 5 wt % n-butenes or n-pentenes can be used in the present method.

ZSM-35 is more particularly described in U.S. Pat. No. 4,016,245, the entire contents of which are incorporated herein by reference.

For present purposes, "ZSM-35" is considered equivalent to its isotypes, which include ferrierite (P. A. Vaughan, Acta Cryst. 21, 983 (1966)); FU-9 (D. Seddon and T. V. Whittam, European Patent B-55,529, 1985); ISI-6 (N. Morimoto, K. Takatsu and M. Sugimoto, U.S. Pat. No. 4,578,259, 1986); monoclinic ferrierite (R. Gramlich-Meier, V. Gramlich and W. M. Meier, Am. Mineral. 70, 619 (1985)); NU-23 (T. V. Whittam, European Patent A-103,981, 1984); and Sr-D (R. M. Barrer and D. J. Marshall, J. Chem. Soc. 1964, 2296 (1964)). Preferably the catalyst comprises ZSM-35 in its hydrogen-exchanged form, HZSM-35.

An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974)

The zeolite catalyst used is preferably at least partly in the hydrogen form, e.g., HZSM-35, but other cations, e.g., rare earth cations, may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g., by heating at over 500° C. for 1 hour or more. The hydrogen form can then be obtained by base exchange with ammonium salts followed by calcination e.g., at 500° C. in air. Other cations, e.g., metal cations, can be introduced by conventional base exchange or impregnation techniques.

The ZSM-35 is incorporated in another material usually referred to as a matrix or binder. Such matrix materials include synthetic or naturally occurring substances as well as inorganic oxide materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant isomerization processes. Alternatively, silica-containing matrix containing a minor amount of aluminum may be employed.

The relative proportions of ZSM-35 and inorganic oxide gel matrix vary with the zeolite content ranging from 5 to 25 or even 40 percent by weight zeolite and more usually in the range of 10 to 20 percent by weight zeolite of the composite.

The regeneration of spent zeolite catalyst used in the isomerization reaction is carried out oxidatively or hydrogenatively employing procedures known in the art. The catalyst of the present invention can be readily reactivated without significantly reducing selectivity for isobutene by exposing it to hydrogen for a suitable period, e.g., overnight.

The use of low zeolite content ZSM-35 catalyst in accordance with the present invention results in less coking of the catalyst, relative to higher zeolite content catalyst. This results in lower end of cycle coke content (wt % coke), reducing regeneration requirements when end of cycle is reached say, e.g. a conversion level below 25–30%. Indeed, the end of cycle coke levels may be reduced by as much as 50 to 80%, or even more, for low zeolite catalysts employed under similar conditions, compared with those for higher zeolite content catalysts.

The examples which follow illustrate the invention without restricting it in any way.

EXAMPLE 1

Preparation of High Zeolite Content ZSM-35 and Low Zeolite Content Catalyst Compositions 1.18 parts of aluminum sulfate (17.2% $Al_2O_3$) were added to a solution containing 9.42 parts $H_2O$ and 1.38 parts of 50% NaOH solution in an autoclave. 0.03 parts of ZSM-35 seeds and 3.20 parts of Hi-Sil precipitated silica were added with agitation, followed by 1.0 part of pyrrolidine.

The reaction mixture had the following composition, in mole ratios:

| | |
|---|---|
| $SiO_2/Al_2O_3$ | 21.5 |
| $OH^-/SiO_2$ | 0.11 |
| $H_2O/Al_2O_3$ | 13.5 |
| $R/Al_2O_3$ | 6.45 | where R=pyrrolidine. The mixture was crystallized at 105° C. for 74 hours with stirring. The ZSM-35 product was filtered, washed with deionized water, and dried at 120° C.

The chemical composition of the product was, in weight percent:

| | |
|---|---|
| $SiO_2$ | 76.7 |
| $Al_2O_3$ | 6.4 |
| Na | 0.84 |
| C | 7.26 |
| N | 2.03 |
| Ash @ 1000° C. | 85.5 | with a silica/alumina ratio for the product, in moles, of 20.3/1.

Scanning electron microscopy and transmission electron microscopy indicate the ZSM-35 crystals have platelet morphology with a broad distribution of crystal sizes having the largest dimension of up to 0.05 to 0.1 micron.

65% ZSM-35/35% $SiO_2$ catalyst was prepared by dry mixing the as-synthesized ZSM-35 zeolite with precipitated silica. Colloidal silica, in proportion to give 65% ZSM-35/35% $SiO_2$ in the catalyst was added to the dry mix, dissolved in sufficient water to obtain an extrudable mull mix which was extruded to 1/20 inch quadrulobe shape and dried at 120° C. The extrudate was twice exchanged with 1N $NH_4NO_3$ solution (5 ml of solution per gram of catalyst) at room temperature, rinsed with deionized water, dried at 120° C., and calcined in nitrogen for three hours at 538° C. It was again exchanged with 1N $NH_4NO_3$ solution twice at room temperature, rinsed with deionized water, dried at 120° C., and calcined in air for eight hours at 538° C.

Low zeolite content ZSM-35 20% ZSM-35/80% $SiO_2$ catalyst was prepared by dry mixing the as-synthesized ZSM-35 zeolite with precipitated silica. Colloidal silica, in proportion to give 20% ZSM-35/80% $SiO_2$ in the catalyst was added to the dry mix, dissolved in sufficient water to obtain an extrudable mull mix which was extruded to 1/10 inch quadrulobe shape and dried at 120° C. The extrudate was twice exchanged with 1N $NH_4NO_3$ solution (5 ml of solution per gram of catalyst) at room temperature, rinsed with deionized water, dried at 120° C., and calcined in nitrogen for three hours at 538° C. It was again exchanged with 1N $NH_4NO_3$ solution twice at room temperature, rinsed with deionized water, dried at 120° C., and calcined in air for eight hours at 538° C.

Low zeolite content ZSM-35 10% ZSM-35/90% $SiO_2$ catalyst was prepared by dry mixing the as-synthesized ZSM-35 zeolite with precipitated silica. Colloidal silica, in proportion to give 10% ZSM-35/90% $SiO_2$ in the catalyst was added to the dry mix, dissolved in sufficient water to obtain an extrudable mull mix which was extruded to 1/20 inch quadrulobe shape and dried at 120° C. The extrudate was twice exchanged with 1N $NH_4NO_3$ solution (5 ml of solution per gram of catalyst) at room temperature, rinsed with deionized water, dried at 120° C., and calcined in nitrogen for three hours at 538° C. It was again exchanged with 1N $NH_4NO_3$ solution twice at room temperature, rinsed with deionized water, dried at 120° C., and calcined in air for eight hours at 538° C.

EXAMPLE 2

Isomerization of 1-Butene with ZSM-35 at 400° C.

Figure 1:
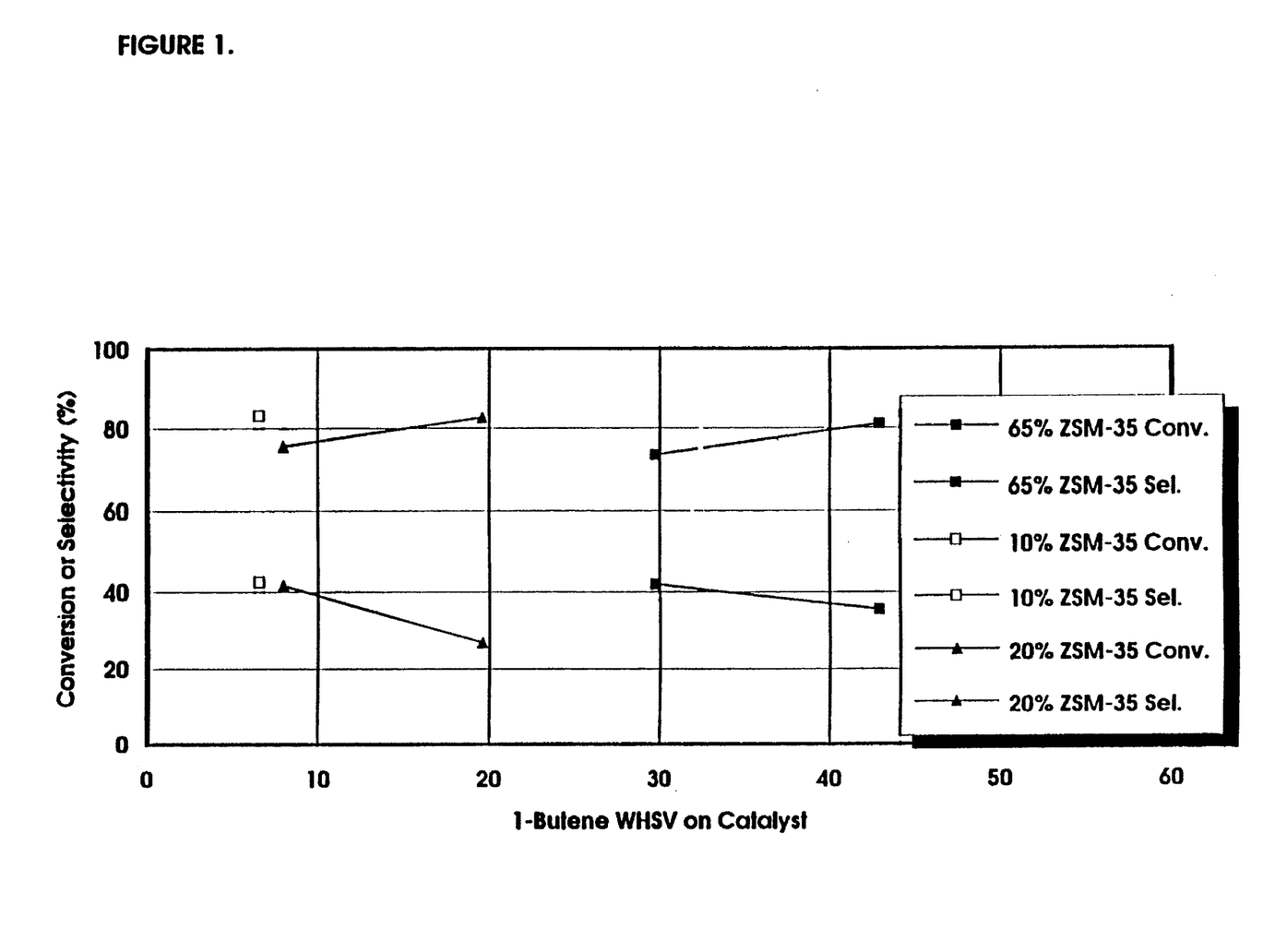
FIG. 1 depicts the effect of ZSM-35 content on catalyst activity in butene skeletal isomerization by comparing conversion and selectivity for both high (65 wt %) and low (10 and 20 wt %) ZSM-35 content catalysts at varying 1-butene WHSV (based on catalyst).

The above-prepared ZSM-35 catalyst composition samples were used in butene skeletal isomerization reactions carried out at 400° C., at a total pressure of 206 kPa (30 psia) using a 1/1 vol/vol 1-butene/nitrogen. The process with low zeolite content (10 wt %) ZSM-35 catalyst was carried out at a WHSV of about 7. The process with low zeolite content (20 wt %) ZSM-35 catalyst was carried out at a WHSV of about 8 as well as at about 19. The process with high zeolite content (65 wt %) ZSM-35 catalyst was carried out at a WHSV of about 30 as well as at about 43. The 1-butene conversion and isobutene selectivity at varying 1-butene WHSV on catalyst are depicted in FIG. 1 at 300 to 600 g cumulative olefin throughput per g catalyst. The experimental results show that catalyst activity can be successfully lowered by reducing zeolite content from 65% to 20% or 10%.

Figure 2:
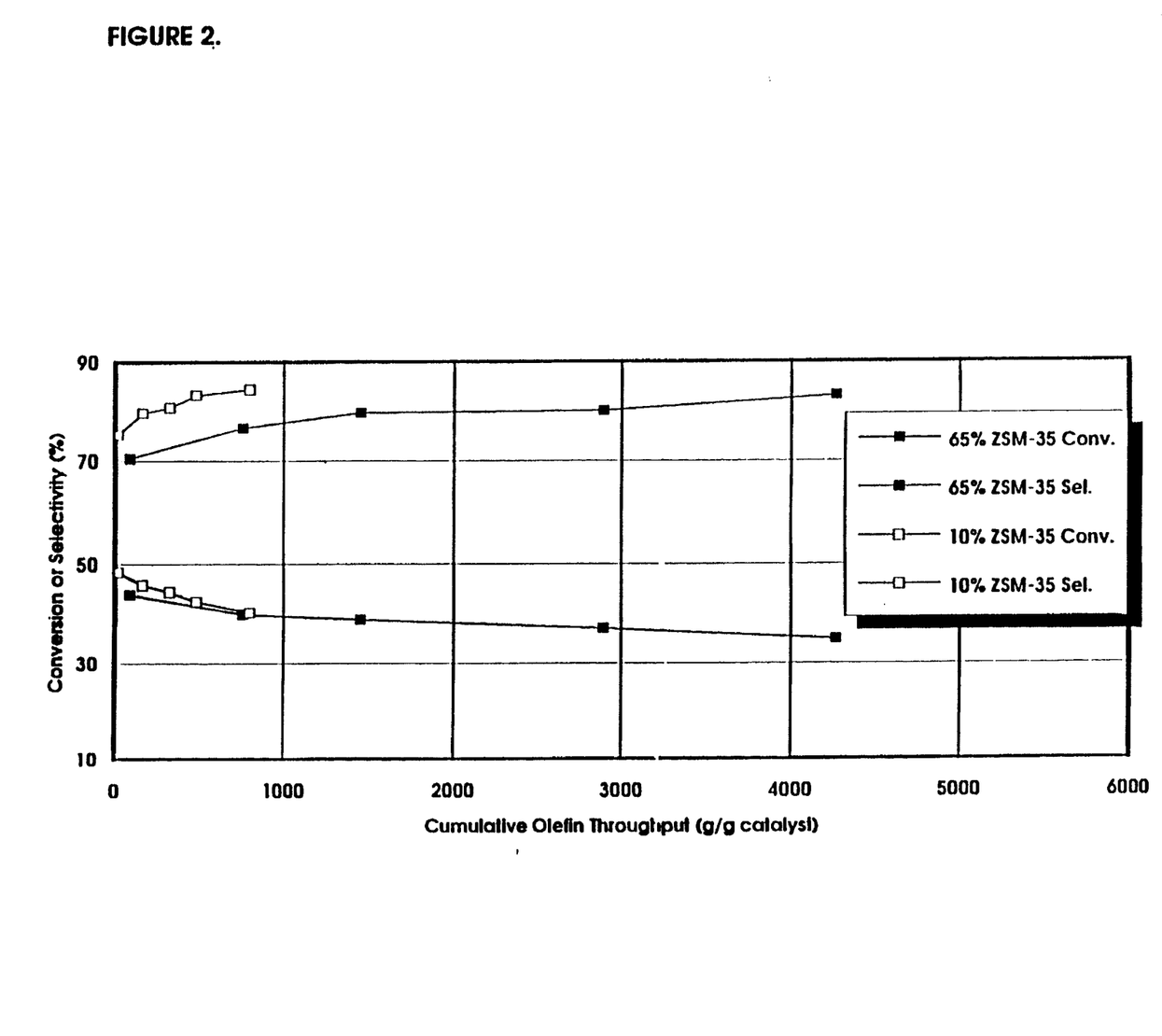
FIG. 2 depicts the effect of zeolite content on conversion and isobutene selectivity in butene skeletal isomerization by comparing conversion and selectivity for both high (65 wt %) and low (10 wt %) zeolite content catalysts versus cumulative olefin throughput (g olefin/g catalyst).

FIG. 2 shows the effect of zeolite content on aging and selectivity of ZSM-35. A comparison between 65% ZSM-35 (at 30 WHSV) and 10% ZSM-35 (at 7 WHSV) wherein the space velocity is selected to provide approximately the same initial conversion shows significantly enhanced iso-olefin selectivity during initial operation (cumulative olefin throughput of 0 to about 800 g/g catalyst). FIG. 2 further shows that reduction in zeolite content does not negatively affect the stability of ZSM-35 catalyst in olefin skeletal isomerization.

Figure 3:
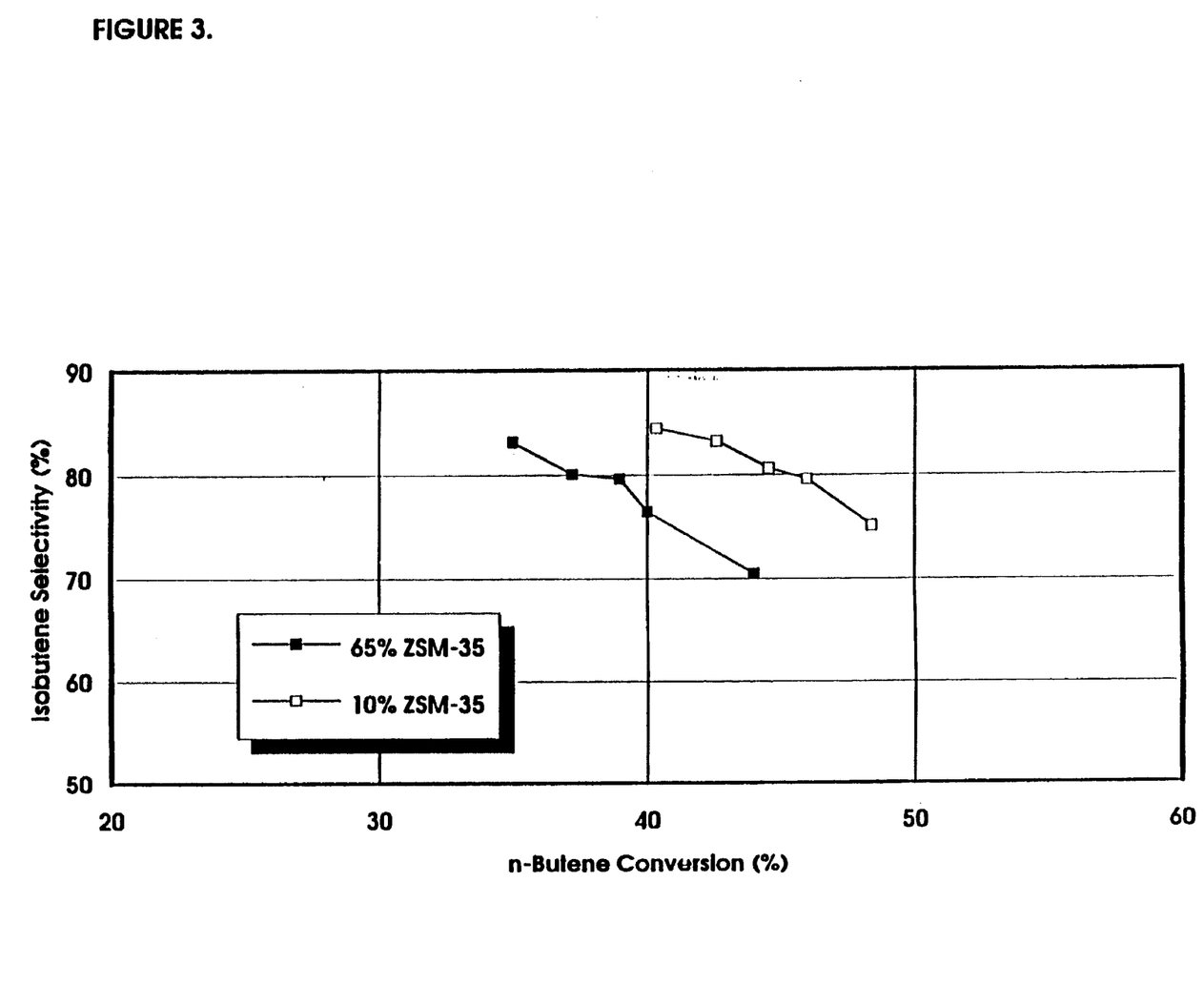
FIG. 3 depicts the effect of zeolite content on isobutene selectivity in butene skeletal isomerization by comparing selectivity versus conversion.

FIG. 3 shows the effect of zeolite content on ZSM-35 catalyst selectivity vs. conversion performance. A comparison between 65% ZSM-35 (at 30 WHSV) and 10% ZSM-35 (at 7 WHSV) catalysts, wherein the space velocity is selected to provide approximately the same initial conversion, shows significantly enhanced iso-olefin selectivity (about 10%) for the low zeolite content ZSM-35 catalyst.

EXAMPLE 3

Figure 4:
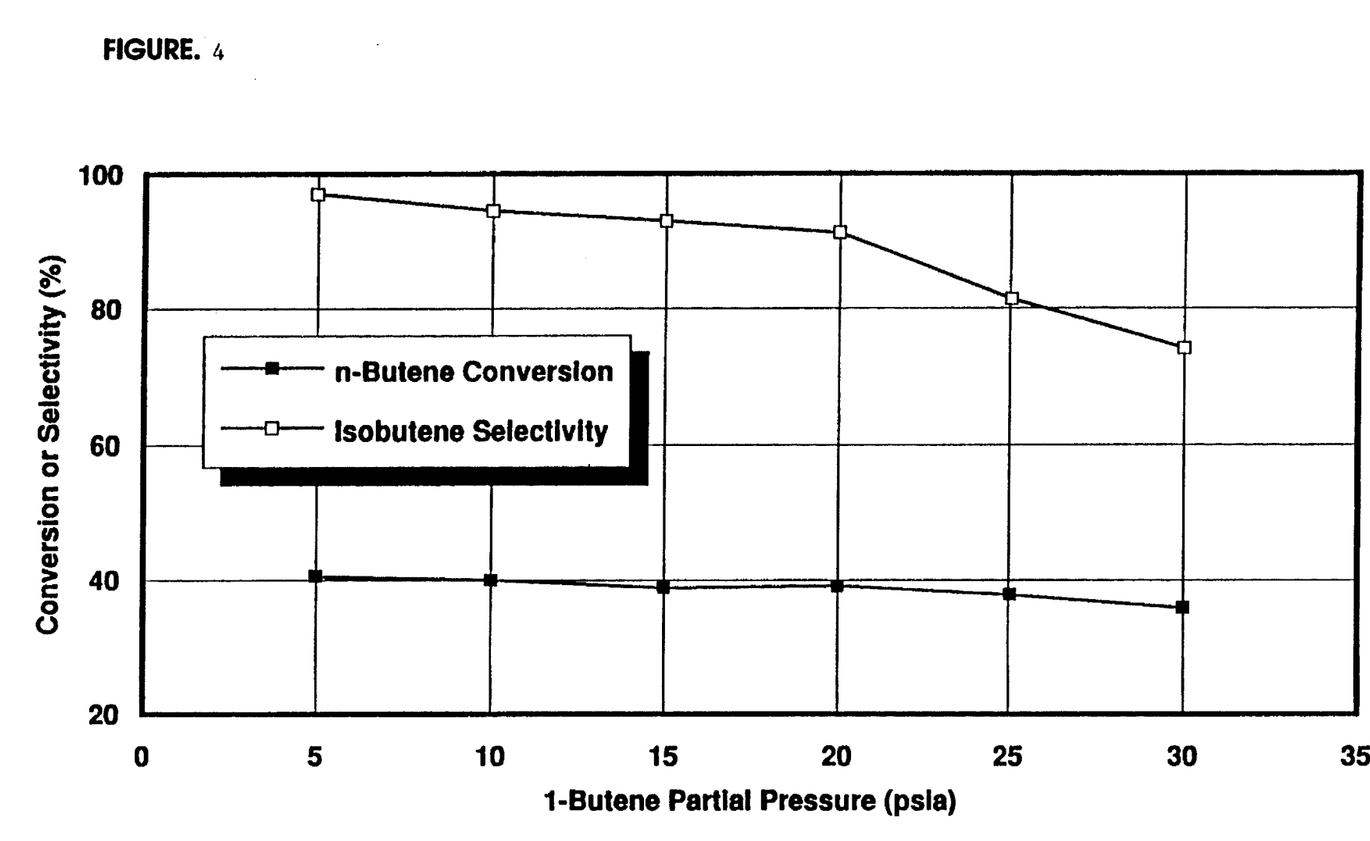
FIG. 4 depicts the effect of linear olefin partial pressure for high (65 wt %) zeolite content catalyst on conversion and isobutene selectivity over a range of 5 to 30 psia 1-butene partial pressure.
Figure 5:
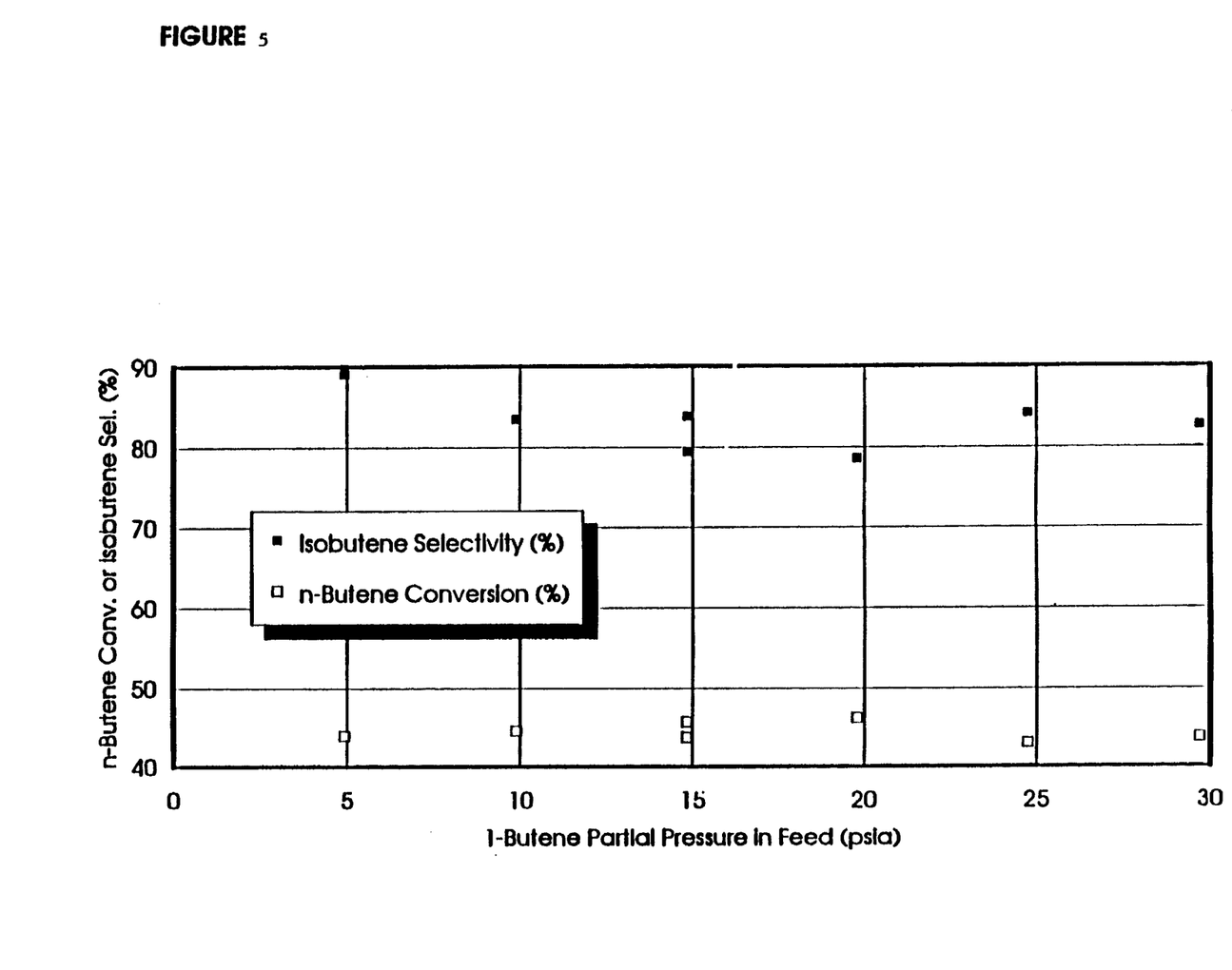
FIG. 5 depicts the effect of linear olefin partial pressure for low (20 wt %) zeolite content catalyst on conversion and isobutene selectivity over a range of 5 to 30 psia 1-butene partial pressure.

Isomerization of 1-Butene with Low Zeolite Content (20%) ZSM-35 Catalyst at 400° C. and Varying 1-Butene Partial Pressure The low zeolite content (20 wt %) ZSM-35 catalyst composition samples were used in butene skeletal isomerization reactions carried out at 400° C., at a total pressure of 206 kPa (30 psia) using a varying vol/vol 1-butene/nitrogen ratio to provide varying butene partial pressure over a range of about 35 to 206 kPa (5 to 30 psia) at 35 kPa (5 psia) increments. Total feed/catalyst contact time was unchanged for all data points at 0.5 second. At 1/1 vol/vol butene/nitrogen feed, the butene on catalyst WHSV was about 10. The results, depicted in FIG. 5, show that the butene skeletal isomerization performance of lower zeolite catalyst content was essentially unaffected by feed butene partial pressure under typical process conditions. In contrast, with 65 wt % zeolite catalyst, selectivity for isobutene deteriorates significantly with increasing feed olefin partial pressure as shown in FIG. 4.

EXAMPLE 4

Isomerization of 1-Butene with Low Zeolite Content (10%) ZSM-35 and High Zeolite Content (65%) ZSM-35 at 400° C. to End of Cycle The lower coking benefit associated with low zeolite content ZSM-35 catalyst was demonstrated by performing runs with the 10% and 65% zeolite catalysts under similar conditions 400° C., 206 kPa (30 psia), 1/1 vol/vol 1-butene/nitrogen feed, 65 1-butene WHSV on zeolite. The runs for the 65% and 10% ZSM-35 catalysts were ended at 6–9 and 10 kg/g zeolite cumulative olefin throughputs, respectively. Analysis determined that the low zeolite content ZSM-35 catalyst had picked up 2–3 wt % coke weight, while the high zeolite content catalyst picked up 11–13 wt % coke.

What is claimed is:

1. A method for conversion of linear olefins to corresponding iso-olefins which comprises contacting a linear olefin-containing organic feedstock with a catalyst comprising a zeolite having the structure of ZSM-35 under skeletal isomerization conditions, wherein said catalyst comprises 5 to 25 wt % of said zeolite, and 75 to 95 wt % silica binder, said method providing reduced coke levels on the catalyst compared with higher zeolite content catalyst.

2. The method of claim 1 wherein said conversion is carried out at temperatures between about 150° and 600° C., weight hourly space velocities (WHSV) based on linear olefins in said feedstock of less than 30, linear olefin partial pressures between 10 and 500 kPa, and conversion levels of at least 25 weight percent, and wherein said catalyst comprises 10 to 20 wt % of said zeolite, and 80 to 90 wt % inorganic oxide binder.

3. The method of claim 2 wherein said temperatures are between about 250° and 500° C., said weight hourly space velocities (WHSV) are between 5 and 30, said linear olefin partial pressure is between 20 and 200 kPa, and conversion levels of at least 30 weight percent.

4. The method of claim 2 wherein said linear olefin partial pressure is between 100 and 200 kPa.

5. The method of claim 1 wherein said organic feedstock comprises at least 5 wt % n-butenes.

6. The method of claim 1 wherein said feedstock comprises $C_4$ to $C_{10}$ linear olefins.

7. The method of claim 1 wherein said feedstock comprises $C_4$ to $C_6$ linear olefins.

8. The method of claim 1 wherein said organic feedstock consists essentially of a $C_4$ hydrocarbon stream.

9. The method of claim 1 wherein said organic feedstock consists essentially of a $C_{4+}$ hydrocarbon stream.

10. The method of claim 1 wherein said organic feedstock comprises at least 5 wt % n-pentenes.

11. The method of claim 1 wherein said organic feedstock consists essentially of a $C_5$ hydrocarbon stream.

12. The method of claim 1 wherein said organic feedstock consists essentially of a $C_{5+}$ hydrocarbon stream.

13. The method of claim 2 wherein said temperature is less than 450° C.

14. A method for conversion of linear olefins to corresponding iso-olefins which comprises contacting a linear olefin-containing organic feedstock with a catalyst comprising a zeolite having the structure of ZSM-35 under skeletal isomerization conditions which comprise linear olefin conversion of at least 25 weight percent, linear olefin partial pressures of greater than 100 kPa and iso-olefin selectivity of greater than 70 wt %, wherein said catalyst comprises 5 to 25 wt % of said zeolite, and 75 to 95 wt % silica binder, said method providing reduced coke levels on the catalyst compared with higher zeolite content catalyst.

15. The method of claim 14 wherein said catalyst comprises 10 to 20 wt % of said zeolite.

16. The method of claim 14 wherein said conditions comprise weight hourly space velocities.

17. The method of claim 14 wherein said conditions comprise weight hourly space velocities.

18. A method for conversion of linear olefins to corresponding iso-olefins which comprises contacting a linear olefin-containing organic feedstock with a catalyst comprising a zeolite having the structure of ZSM-35 under skeletal isomerization conditions which comprise weight hourly space velocities (WHSV) based on linear olefins in said feedstock of less than 30 wherein said catalyst comprises 5 to 25 wt % of said zeolite, and 75 to 95 wt % silica binder, said method providing reduced coke levels on the catalyst compared with higher zeolite content catalyst.

* * * * *

UNITED STATES PATENT AND TRADEMARK OFFICE
CERTIFICATE OF CORRECTION

PATENT NO. : 5,523,511
DATED : June 4, 1996
INVENTOR(S) : Claus-Peter Haelsig, et al.

It is certified that error appears in the above-indentified patent and that said Letters Patent is hereby corrected as shown below:

Col. 10, line 45, after "velocities" insert --(WHSV) based on linear olefins in said feedstock of less than 30.--

Col. 10, line 38, after "velocities" insert --(WHSV) based on linear olefins in said feedstock of less than 30.--

Signed and Sealed this

Third Day of September, 1996

Attest:

BRUCE LEHMAN

Attesting Officer

Commissioner of Patents and Trademarks